United States Patent [19]

Peterson

[11] 4,142,052

[45] Feb. 27, 1979

[54] ω-ARYL-PGD COMPOUNDS

[75] Inventor: David C. Peterson, Portage, Mich.

[73] Assignee: The Upjohn Company, Kalamazoo, Mich.

[21] Appl. No.: 809,249

[22] Filed: Jun. 23, 1977

Related U.S. Application Data

[62] Division of Ser. No. 614,244, Sep. 17, 1975.

[51] Int. Cl.$^2$ ............................................. C07C 177/00
[52] U.S. Cl. ....................................... 560/53; 562/463
[58] Field of Search ........................... 560/53; 562/463

[56] References Cited

FOREIGN PATENT DOCUMENTS 2507425  2/1976  Fed. Rep. of Germany ............. 560/53

OTHER PUBLICATIONS

Derwent Abstr. 68902X/37, 02-09-76, DT 2507425.
Derwent Abstr. 24068Y/14, 21-03-77, NL 7610184.
Derwent Abstr. 29127Y/17, 22-04-77, BE 847.548.
Derwent Abstr. 81216X/44, 18-10-76, BE 840.871.

Primary Examiner—Paul J. Killos
Attorney, Agent, or Firm—Robert A. Armitage

[57] ABSTRACT

Prostaglandin analogs with the following cyclopentane ring structure:

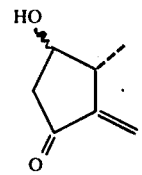

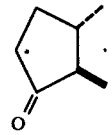

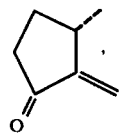

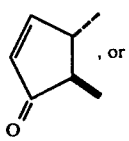

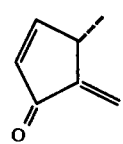

are disclosed along with intermediates useful in their preparation and processes for their preparation. These analogs are useful for some of the same pharmacological purposes as the prostaglandins, particularly and especially as blood platelet aggregation inhibitors.

77 Claims, No Drawings

ω-ARYL-PGD COMPOUNDS

The present application is a divisional application of Ser. No. 614,244, filed Sept. 17, 1975, now pending. Likewise, U.S. Ser. No. 809,248, filed June 23, 1977 is a divisional application of Ser. No. 614,244.

The present invention relates to prostaglandin analogs for which the essential material constituting a disclosure therefor is incorporated by reference here from Ser. No. 809,248, now U.S. Pat. No. 4,099,014.

I claim:

1. A prostaglandin analog of the formula

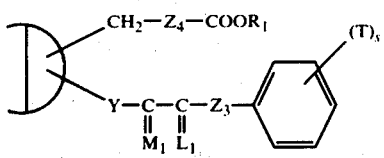

wherein D is

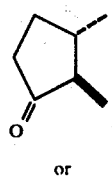

or

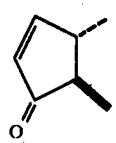

wherein Y is cis—CH=CH—, trans—CH=CH—, or —CH$_2$CH$_2$—;
wherein Z$_4$ is
  (1) cis—CH=CH—CH$_2$—(CH$_2$)$_g$—CF$_2$—,
  (2) cis—CH=CH—CH$_2$—(CH$_2$)$_g$—CH$_2$—,
  (3) cis—CH$_2$—CH=CH—(CH$_2$)$_g$—CH$_2$—,
  (4) —(CH$_2$)$_3$—(CH$_2$)$_g$—CF$_2$—, or
  (5) —(CH$_2$)$_3$—(CH$_2$)$_g$—CH$_2$—,
  wherein g is one, 2, or 3;
wherein M$_1$ is

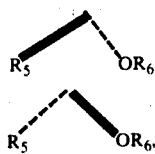

wherein R$_5$ and R$_6$ are hydrogen or methyl, with the proviso that one of R$_5$ and R$_6$ is methyl only when the other is hydrogen;
wherein L$_1$ is

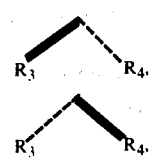

or a mixture of

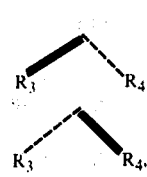

wherein R$_3$ and R$_4$ are hydrogen, methyl, or fluoro, being the same or different, with the proviso that one of R$_3$ and R$_4$ is hydrogen or fluoro only when the other is hydrogen or fluoro;
wherein Z$_3$ is oxa or methylene;
wherein T is chloro, fluoro, trifluoromethyl, alkyl of one to 3 carbon atoms, inclusive or alkoxy of one to 3 carbon atoms, inclusive, and s is zero, one, 2, or 3, the various T's being the same or different, with the proviso that not more than two T's are other than alkyl, with the further proviso that Z$_3$ is oxa only when R$_3$ and R$_4$ are hydrogen or methyl, being the same or different; and
wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation;
with the further proviso that D is

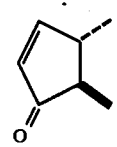

only when Y is —CH$_2$CH$_2$—.

2. A compound according to claim 1, wherein M$_1$ is

3. A compound according to claim 1, wherein M$_1$ is

4. A compound according to claim 3, wherein D is

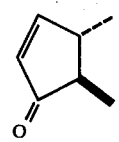

and Y is —CH$_2$CH$_2$—.

5. A compound according to claim 4, wherein Z$_3$ is methylene.

6. A compound according to claim 5, wherein s is zero or one and T is chloro, fluoro, or trifluoromethyl.

7. A compound according to claim 6, wherein Z$_4$ is cis—CH=CH—CH$_2$—(CH$_2$)$_g$—CF$_2$—.

8. A compound according to claim 7, wherein g is one.

9. A compound according to claim 8, wherein R$_5$ and R$_6$ are both hydrogen.

10. A compound according to claim 9, wherein $R_3$ and $R_4$ are both hydrogen.

11. 2,2-Difluoro-17-phenyl-18,19,20-trinor-13,14-dihydro-9,10-didehydro-9-deoxy-PGD$_2$, a compound according to claim 10.

12. A compound according to claim 6, wherein $Z_4$ is cis—CH=CH—CH$_2$—(CH$_2$)$_g$—CH$_2$—.

13. A compound according to claim 12, wherein g is 3.

14. A compound according to claim 13, wherein $R_5$ and $R_6$ are both hydrogen.

15. A compound according to claim 14, wherein $R_3$ and $R_4$ are both hydrogen.

16. 2a,2b-Dihomo-17-phenyl-18,19,20-trinor-13,14-dihydro-9,10-didehydro-9-deoxy-PGD$_1$; a compound according to claim 15.

17. A compound according to claim 12, wherein g is one.

18. A compound according to claim 17, wherein $R_5$ and $R_6$ are both hydrogen.

19. A compound according to claim 18, wherein $R_3$ and $R_4$ are both hydrogen.

20. 17-Phenyl-18,19,20-trinor-13,14-dihydro-9,10-didehydro-9-deoxy-PGD$_2$, a compound according to claim 19.

21. A compound according to claim 6, wherein $Z_4$ is cis—CH$_2$—CH=CH—(CH$_2$)$_g$—CH$_2$—.

22. A compound according to claim 21, wherein g is one.

23. A compound according to claim 22, wherein $R_5$ and $R_6$ are both hydrogen.

24. A compound according to claim 23, wherein $R_3$ and $R_4$ are both hydrogen.

25. cis-4,5-Didehydro-17-phenyl-18,19,20-trinor-13,14-dihydro-9,10-didehydro-9-deoxy-PGD$_1$, a compound according to claim 24.

26. A compound according to claim 6, wherein $Z_4$ is —(CH$_2$)$_3$—(CH$_2$)$_g$—CF$_2$—.

27. A compound according to claim 26, wherein g is one.

28. A compound according to claim 27, wherein $R_5$ and $R_6$ are both hydrogen.

29. A compound according to claim 28, wherein $R_3$ and $R_4$ are both hydrogen.

30. 2,2-Difluoro-17-phenyl-18,19,20-trinor-13,14-dihydro-9,10-didehydro-9-deoxy-PGD$_1$, a compound according to claim 29.

31. A compound according to claim 6, wherein $Z_4$ is —(CH$_2$)$_3$—(CH$_2$)$_g$—CH$_2$—.

32. A compound according to claim 31, wherein g is 3.

33. A compound according to claim 32, wherein $R_5$ and $R_6$ are both hydrogen.

34. A compound according to claim 33, wherein $R_3$ and $R_4$ are both hydrogen.

35. 2a,2b-Dihomo-17-phenyl-18,19,20-trinor-13,14-dihydro-9,10-didehydro-9-deoxy-PGD$_1$, a compound according to claim 34.

36. A compound according to claim 31, wherein g is one.

37. A compound according to claim 36, wherein $R_5$ and $R_6$ are both hydrogen.

38. A compound according to claim 37, wherein $R_3$ and $R_4$ are both hydrogen.

39. 17-Phenyl-18,19,20-trinor-13,14-dihydro-9,10-didehydro-9-deoxy-PGD$_1$, a compound according to claim 38.

40. A compound according to claim 4, wherein $Z_3$ is oxa.

41. A compound according to claim 40, wherein s is zero or one and T is chloro, fluoro, or trifluoromethyl.

42. A compound according to claim 41, wherein $Z_4$ is cis—CH=CH—CH$_2$—(CH$_2$)$_g$—CF$_2$—.

43. A compound according to claim 42, wherein $R_5$ and $R_6$ are both hydrogen.

44. A compound according to claim 43, wherein $R_3$ and $R_4$ are both hydrogen.

45. 2,2-Difluoro-16-phenoxy-17,18,19,20-tetranor-13,14-dihydro-9,10-didehydro-9-deoxy-PGD$_2$, a compound according to claim 44.

46. A compound according to claim 41, wherein $Z_4$ is cis—CH=CH—CH$_2$—(CH$_2$)$_g$—CH$_2$—.

47. A compound according to claim 46, wherein g is 3.

48. A compound according to claim 47, wherein $R_5$ and $R_6$ are both hydrogen.

49. A compound according to claim 48, wherein $R_3$ and $R_4$ are both hydrogen.

50. 2a,2b-Dihomo-16-phenoxy-17,18,19,20-tetranor-13,14-dihydro-9,10-didehydro-9-deoxy-PGD$_2$, a compound according to claim 49.

51. A compound according to claim 46, wherein g is one.

52. A compound according to claim 51, wherein $R_5$ and $R_6$ are both hydrogen.

53. A compound according to claim 52, wherein $R_3$ and $R_4$ are both hydrogen.

54. 16-Phenoxy-17,18,19,20-tetranor-13,14-dihydro-9,10-didehydro-9-deoxy-PGD$_2$, a compound according to claim 53.

55. A compound according to claim 41, wherein $Z_4$ is cis—CH$_2$—CH=CH—(CH$_2$)$_g$—CH$_2$—.

56. A compound according to claim 55, wherein g is one.

57. A compound according to claim 56, wherein $R_5$ and $R_6$ are both hydrogen.

58. A compound according to claim 57, wherein $R_3$ and $R_4$ are both hydrogen.

59. A compound according to claim 3, wherein D is

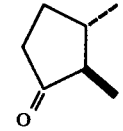

60. A compound according to claim 59, wherein $Z_3$ is methylene.

61. A compound according to claim 60, wherein s is zero or one and T is chloro, fluoro, or trifluoromethyl.

62. A compound according to claim 61, wherein $Z_4$ is cis—CH=CH—CH$_2$—(CH$_2$)$_g$—CF$_2$—, cis—CH=•CH—CH$_2$—(CH$_2$)$_g$—CH$_2$—, or cis—CH$_2$—CH=•CH—(CH$_2$)$_g$—CH$_2$—.

63. A compound according to claim 62, wherein g is one.

64. A compound according to claim 63, wherein $R_5$ and $R_6$ are both hydrogen.

65. A compound according to claim 64, wherein $R_3$ and $R_4$ are both hydrogen.

66. 2,2-Difluoro-17-phenyl-18,19,20-trinor-9-deoxy-PGD$_2$, a compound according to claim 65.

67. 17-Phenyl-18,19,20-trinor-9-deoxy-PGD$_2$, a compound according to claim 65.

68. cis-4,5-Didehydro-17-phenyl-18,19,20-trinor-9-deoxy-PGD$_1$, a compound according to claim 65.

69. A compound according to claim 59, wherein Z$_3$ is oxa.

70. A compound according to claim 69, wherein s is zero or one and T is chloro, fluoro, or trifluoromethyl.

71. A compound according to claim 70, wherein Z$_4$ is cis—CH=CH—CH$_2$—(CH$_2$)$_g$—CF$_2$—, cis—CH=CH—CH$_2$—(CH$_2$)$_g$—CH$_2$—, or cis—CH$_2$—CH=CH—(CH$_2$)$_g$—CH$_2$—.

72. A compound according to claim 71, wherein g is one.

73. A compound according to claim 72, wherein R$_5$ and R$_6$ are both hydrogen.

74. A compound according to claim 73, wherein R$_3$ and R$_4$ are both hydrogen.

75. 2,2-Difluoro-16-phenoxy-17,18,19,20-tetranor-9-deoxy-PGD$_2$, a compound according to claim 74.

76. 16-Phenoxy-17,18,19,20-tetranor-9-deoxy-PGD$_2$, a compound according to claim 74.

77. cis-4,5-Didehydro-16-phenoxy-17,18,19,20-tetranor-9-deoxy-PGD$_1$, a compound according to claim 74.

* * * * *